United States Patent [19]
Masterson

[11] Patent Number: 6,054,261
[45] Date of Patent: Apr. 25, 2000

[54] COENZYME $Q_{10}$ COMPOSITIONS FOR ORGAN PROTECTION DURING PERFUSION

[75] Inventor: Robert V. Masterson, Vashon Island, Wash.

[73] Assignee: Q-pharma, Inc., Edmonds, Wash.

[21] Appl. No.: 09/082,133

[22] Filed: May 20, 1998

[51] Int. Cl.$^7$ ................................................. A01N 1/00
[52] U.S. Cl. ...................................... 435/1.2; 514/675
[58] Field of Search .............................. 435/1.2; 514/675

[56] References Cited

FOREIGN PATENT DOCUMENTS 522433   1/1993   European Pat. Off. .

OTHER PUBLICATIONS

Valls et al., "Potective Effect of Exogenous Coenzyme Q Against Damage by Adriamycin in Perfused Rat Liver", Biochemistry and Molecular Biology International 33 : 633–42 (1994).

Mori et al., "Effects of Coenzyme Q10 Added to a Potassium Cardioplegic Solution for Myocardial Protection during Ischemic Cardiac Arrest",Annals of Thoracic Surgery 39 : 30–6 (1985).

Yamamoto et al., "Potentiating Effect of Coenzyme Q on Root Potentials of Perfused Frog's Spinal Cord" Japan. J. Pharmacol. 22 : 707–14 (1972).

Handa et al., "Formation and Structure of Stably Dispersed Small Particles Composed of Phosphatidylcholine and Ubiquinone–10", J. Colloid Interface Sci. 143 : 205–13 (1991).

Kimura et al., "Factors Influencing the Tissue Distribution of Coenzyme Q10 Intravenously Administered in an Emulsion to Rats:Emulsifying Agents and Lipoprotein Lipase Activity" J. Pharm. Pharmacol. 38 : 659–62 (1986).

Julia et al., "Studies of controlled reperfusion after ischemia XXI" J. Thorac. Cardiovasc. Surg. 101 : 303–13 (1991).

Gunstone et al., The Lipid Handbook, second edition. Chapman & Hall, 1994, p. 99.

*Primary Examiner*—Sandra E. Saucier
*Attorney, Agent, or Firm*—Townsend and Townsend and Crew

[57] ABSTRACT

The present invention describes compositions and methods for use when an organ is isolated from the circulatory system, i.e., in organ transplantation and surgery. The composition of the present invention uses an organ preservation or perfusion solution to which is added a Coenzyme $Q_{10}$ in a solubilizing agent. The solubilizing agent of the present invention is capable of solubilizing Coenzyme $Q_{10}$, is non-toxic to organ tissues and cells, and is compatible with organ perfusion devices. When used in an organ perfusion the compositions of the Coenzyme $Q_{10}$ does not precipitate from the compositions of the present invention. Particularly, the solubilizing agents are polysorbates, such as polysorbate-80 (polyoxyethzlene (20) sorbitan mono-oleate) or phosphatides, such as lecithin, and the like. Methods are also provided for using the compositions of the present invention to protect organs from free radical damage, ischemia and reperfusion injury during organ transplant and surgery.

19 Claims, No Drawings

COENZYME $Q_{10}$ COMPOSITIONS FOR ORGAN PROTECTION DURING PERFUSION

BACKGROUND OF THE INVENTION

An important component of respiration Coenzyme $Q_{10}$ (2,3-dimethoxy-3-methy-6-decaprenyl-1,4-benzoquinone), also known as ubiquinone, is located in the mitochondria of eukayotes. Coenzyme $Q_{10}$ is essential for electron transport, oxidative phosphorylation and it is an effective antioxidant. Experiments have shown that Coenzyme $Q_{10}$ is beneficial to organs, including hearts, when supplied orally to whole animals. For example, Folkers et al., *Proc. Natl. Acad. Sci.* 82:4513 (1985) have shown beneficial results with human hearts after oral consumption of Coenzyme $Q_{10}$. Furthermore, isolated organs have benefited from the administration of Coenzyme $Q_{10}$ prior to isolation (Sumitomo et al., *Surgery* 102:821–827 (1987); and Matsushima et al., *J. Thorac. Cardiovasc. Surg.* 103:945–951 (1992).

Successful organ transplantation is often limited due to ischemic/reperfusion injury. Isolated human hearts deprived of oxygen for more than four hours progressively loose vigor and often do not survive in recipient hosts. Other organs such as the kidney, liver, pancreas and lung are also subject to tissue and cellular damage when removed from their hosts prior to transplantation. This damage is due to hypoxic conditions and a lack of circulation, which normally delivers physiological concentrations of oxygen and nutrients, and removes toxic compounds produced by an organ's cells. Organ transplants have a higher frequency of success when performed immediately after excision from their hosts.

Two recent advances have increased the rate of successful organ transplants and organ surgery, such as coronary bypass surgery. The first includes organ preservation and organ perfusion solutions. The second is improved methods and devices for the delivery of organ perfusion solutions to an organ.

Organs other than hearts can be stored for extended periods prior to transplantation when maintained in an organ preservation solution. Surgery involving organs, such as coronary bypass surgery, requires preservation solutions, i.e., a cardioplegic solution, which help preserve the heart during hypoxic conditions when the heart is stopped. Organ preservation and cardioplegic solutions include Krebs-Henseleit solution, UW solution, St. Thomas II solution, Collins solution and Stanford solution. (See, for example, U.S. Pat. Nos. 4,798,824; 4,938,961; Southard and Belzer, *Ann. Rev. Med.* 46:235–247 (1995); and Donnelly and Djuric, *Am. J. Hosp. Pharm.* 48:2444–2460 (1991)).

Organ perfusion devices, such as those described by Sadri (U.S. Pat. Nos. 5,338,662 and 5,494,822), are designed to provide a continuous flow of nutrients, containing physiological concentrations of oxygen, through the vascular tissues of organs including the heart, lung, kidney, liver and pancreas. Drugs and other chemicals can also be delivered to organs using these devices. Perfusion of organs with a perfusion solution provides conditions that more closely resemble the in vivo situation in which organs normally function. Toxic byproducts are flushed from organs by a continuous flow of perfusate solution. Furthermore, organ perfusion can be performed with organs in vitro and in vivo. Therefore, more optimal conditions for organs subjected to transplantation and surgery, such as coronary bypass surgery, are available using an organ perfusion device together with an organ perfusate solution.

Organ perfusion utilizing an organ perfusion device requires a steady flow and delivery of a perfusate solution to an organ. Additives to perfusate solutions, such as drugs, are optimally effective when thoroughly dissolved. Large, undissolved or globular chemical moieties are undesirable in these solutions due to small capillary size and strong shear forces that occur during perfusion through organ tissues. Delivery of highly concentrated chemicals to organs undergoing perfusion, can occur if the chemicals are not dissolved or are aggregated in large particles. Separation or precipitation of the chemical from the perfusion solution while passing through an organ can lead to toxic side effects. Therefore, drugs and other additives to perfusate solutions are best supplied in a soluble form.

Coenzyme $Q_{10}$ is insoluble in water, which is the main constituent of organ perfusion and organ preservation solutions. Experiments with whole animals and isolated organs have demonstrated the protective effects of Coenzyme $Q_{10}$ and have been conducted with undissolved Coenzyme $Q_{10}$, Coenzyme $Q_{10}$ dissolved in water-based solutions, and Coenzyme $Q_{10}$ dissolved in soybean oil (Folkers et al., *Proc. Natl. Acad. Sci. USA* 82:4513–4516 (1985); Tatsukawa et al., *Life Sci.* 24:1309–1314 (19); and Hanioka et al., *Molec. Aspects Med.* 15:241–248 (1994)). Likewise, isolated organs have been shown to gain protection from ischemia/reperfusion injury when treated with Coenzyme $Q_{10}$ (Mori et al. *Ann. Thorac. Surg.* 39:30–36 (1985)).

However, none of these presentations of Coenzyme $Q_{10}$ are appropriate for use with organ perfusion device systems due to the instability of the fatty emulsion leading to the insolubility of Coenzyme $Q_{10}$ in water, organ preservation solutions and cardioplegia solutions. In particular, Coenzyme $Q_{10}$ can precipitate during perfusion of an organ from the water-based nutrient media during circulation and can be detrimental should insoluble Coenzyme $Q_{10}$ crystals block the capillary beds.

Coenzyme $Q_{10}$ solubilized in vegetable oil, and the like, is not suitable for use with many organ perfusion devices because the oil can separate from the aqueous phase during passage of perfusate solution through the device. Separated vegetable oil forms large, globular moieties that are undesirable for organ tissues undergoing perfusion. Once the oil separates, Coenzyme $Q_{10}$ which can remain, at least partially, dissolved in the oil globules can coat perfusion equipment, including tubing materials, resulting in poor delivery, or the delivery of variable unknown quantities, of Coenzyme $Q_{10}$ to the perfused organ. Therefore, it is of vital importance for organs undergoing perfusion that Coenzyme $Q_{10}$ be used in a solubilized form that is compatible with organ perfusion systems. The present invention unexpectedly fulfills this and other related needs.

SUMMARY OF THE INVENTION

The present invention provides compositions for protecting organ cells and tissues from damage during transplantation or organ bypass surgery. The compositions protect the organ tissues and cells from oxidative damage, ischemia and reperfusion injury while the organ is removed from the normal body circulation and is being bathed with a perfusion solution.

In one embodiment, the compositions of the present invention comprises a perfusion solution, further comprising from about 0.1 to about 100 mg Coenzyme $Q_{10}$ per liter of perfusion solution. The Coenzyme $Q_{10}$ is rendered soluble in the perfusion solution by adding a non-toxic solubilizing agent which is compatible for use with a perfusion device. In a preferred embodiment, the non-toxic solubilizing agent is a polysorbate or lecithin. It is particularly preferred that the polysorbate is polysorbate 80 or polysorbate 20 and is present from about 0.2 to about 20 $\mu$l per liter (v/v) of perfusion solution. Compositions comprising lecithin are preferred to contain from about 10 to about 100 mg of lecithin per liter of perfusion solution.

Perfusion solutions of the present invention can be a cardioplegia solution which is used to bath the heart while it is stopped during, for example, coronary bypass surgery. The perfusion solution can also be an organ preservation solution used to protect an isolated organ from damage prior to transplantation. A particularly, preferred perfusion solution of the present invention include, but is not limited to Krebs-Henseleit solution, University of Wisconsin solution, St. Thomas II solution, Collins solution and Stanford solution.

In a particularly preferred composition the perfusion solution is Krebs-Henseleit solution further comprising 10 mg/l Coenzyme $Q_{10}$ and 2 $\mu$l polysorbate-80 per liter perfusion solution which has been adjusted to a pH of about 7.1 to about 7.6.

In another embodiment of the present invention, methods are provided for protecting organ tissues and cells from damage during perfusion by contacting the organ tissues and cells with a composition comprising a perfusion solution further comprising about 0.1 to about 100 mg Coenzyme $Q_{10}$ per liter perfusion solution and a non-toxic solubilizing agent. The solubilizing agent is preferred to be a polysorbate or lecithin and is present in the perfusion solution as provided above.

The methods of the present invention comprise contacting the organ tissues and cells with a perfusion solution of the present invention during transplantation or surgery to protect the organ tissues and cells from oxidation, ischemia and reperfusion injury. Contact with the perfusion solution can be carried out with a perfusion device. The device can be a reservoir for holding the perfusion solution connected to a vein and/or artery of the organ by a tube or cannula. In one preferred method of the present invention, the reservoir is a syringe.

The perfusion device, in another embodiment of the present invention, is an electrically driven and controlled device which can include various pumps and temperature control devices for delivery of perfusion solution at a controlled volume and temperature. A particular, electrically driven and controlled device, is a heart-lung machine, such as the Life Sustainer 1000™. The methods of the present invention provide a perfusion solution containing solubilized Coenzyme $Q_{10}$ compatible with a perfusion device, and which does not precipitate or aggregate during perfusion through the organ improving the ability of the Coenzyme $Q_{10}$ to protect the perfused organ from damage while isolated from the circulatory system.

DESCRIPTION OF THE SPECIFIC EMBODIMENTS

The present invention describes compositions for solubilizing Coenzyme $Q_{10}$ such that the resulting mixture is compatible with perfusate solutions and perfusion devices, and furthermore is non-toxic to organs. The composition of Coenzyme $Q_{10}$ together with specific solubilizing agents can confer protection to isolated organs from oxidative stress, which can occur after organs are separated from their hosts. Thus, organs undergoing perfusion can receive a perfusate solution containing a composition comprising Coenzyme $Q_{10}$ that is optimized for use with an organ perfusion device.

Coenzyme $Q_{10}$ dissolved with specific solubilizing agents can then be diluted and mixed together with various water-based perfusate solutions. Such perfusate solutions can then be circulated through an organ perfusion device such that organs can receive concentrations of solubilized Coenzyme $Q_{10}$. The perfusate solution can be perfused through the organ and recirculated, or fresh perfusate can be added each time without recirculation.

Coenzyme $Q_{10}$ (2,3-dimethoxy-3-methy-6-decaprenyl-1, 4-benzoquinone) ubiquinone, is a member of a group of lipid-soluble benzoquinones involved in electron transport in mitochondria. The ubiquinones are found in the majority of aerobic organisms. The most preferred ubiquinone for use in the compositions of the present invention is Coenzyme $Q_{10}$.

The compositions of the present invention comprise Coenzyme $Q_{10}$ combined with a solubilizing agent. As used in the present invention, the solubilizing agent must be capable of fully solubilizing Coenzyme $Q_{10}$ in a water based solution (i.e., an organ perfusion or preservation solution). Also, the solubilizing agent must be nondestructive of cells and organs (non-toxic). Further, the solubilizing agent must be compatible with an organ perfusion device. By compatible is meant that the solubilizing agent must be capable of remaining dissolved in the water based solution during passage through the perfusion device without separating from the water solution. Also, the solubilizing agent must be capable of preventing Coenzyme $Q_{10}$ from precipitating or aggregating during passage through the perfusion device because precipitation of the Coenzyme $Q_{10}$ from the perfusion solution can cause damage to the perfused organ.

Preferred solubilizing agents for use in the present invention include polysorbate-80 (polyoxyethylenesorbitan monostearate, Tween-80) and other preparations of polyoxyethylene sorbitan monostearate including polysorbate-20 (Tween-20), and related compounds. The solubilizing agents of the present invention can also act as an emulsifier and defoamer which is particularly desirable for use with an organ perfusion device. Another suitable solubilizing agent for use in the present invention is lecithin (phosphatidylcholine).

Coenzyme $Q_{10}$ is readily available and for example, is manufactured by Kaneka Co., Osaka, Japan. It is also readily available from a number of suppliers. Polysorbate-80, polysorbate-20, and lecithin can be obtained, for example, from Sigma Co., St. Louis, Mo. and are readily available from other suppliers.

Concentrated Coenzyme $Q_{10}$ in polysorbate-80, or together with lecithin, is ideal for dilution with perfusate solutions. Coenzyme $Q_{10}$ remains solubilized after dilution and is able to confer oxidation protection to organs from ischemic/reperfusion stress while undergoing perfusion. Thus, perfused organs which have been exposed to circulating perfusate solutions containing diluted Coenzyme $Q_{10}$-polysorbate-80 or Coenzyme $Q_{10}$-lecithin are protected from oxidative damage. Other solubilizing agents that are compatible with Coenzyme $Q_{10}$ and are otherwise nontoxic to organs can be used as well.

The solubilized Coenzyme $Q_{10}$ of the present invention can be added to organ preservation or organ perfusion media to improve the ability of these solutions to protect and preserve organs during organ transplant or surgery. In particular, the organ preservation or organ perfusion media can be a cardioplegia solution. A cardioplegia solution is a water based solution that is used to stop the heart during, for example, coronary by-pass surgery by selectively increasing potassium concentrations and by inducing hypothermic conditions. These solutions are usually maintained at a temperature of about 4 to 8° C. and contain a potassium salt, i.e., potassium chloride, and are adjusted to a specific pH range. Blood-based cardioplegia solutions are also available. Cardioplegia solutions are designed to protect the heart from ischemic damage and to help minimize injury from reperfusion (Donnelly and Djuric, supra). Examples of organ preservation and organ perfusion media include: Krebs-Henseleit solution, UW solution, St. Thomas II solution, Collins solution, Stanford solution or another solution known in the art. See, for example, U.S. Pat. Nos. 4,798,824; 4,938,961; Ann. Rev. Med. 46:235–247 (1995); and Donnelly and Djuric, Am. J. Hosp. Pharm. 48:2444–2460 (1991); all incorporated herein by reference.

Perfusion solutions for use in the present invention will contain from about 0.1 to about 100 mg Coenzyme $Q_{10}$ will be about 10 mg per liter of perfusion solution. The Coenzyme $Q_{10}$ can be solubilized with about 0.2 to about 20 $\mu l$ solubilizing agent per liter (v/v) of perfusate. About 2 $\mu l$ of polysorbate-80 per liter of perfusion solution is particularly preferred. Lecithin can also be used to achieve similar results when used from about 0.1 to about 100 mg per liter of perfusate to solubilize the Coenzyme $Q_{10}$.

The perfusion media or solution of the present can be used in perfusion devices during surgery. A perfusion device as used herein is any mechanical device which can be used to infuse an organ with the perfusion solution. Such a device can include a reservoir (i.e., a syringe) with a tube or cannula which can be inserted into an organ, vein or artery, or it can be an electrical/mechanical device having electric pumps and devices for controlling the temperature of the perfusion solution. In particular, such an electrical/mechanical perfusion device can be, for example, the Life Sustainer 1000™ (Bio-Preserve Medical Corporation, Redmond, Wash.).

The perfusion solutions of the present invention containing Coenzyme $Q_{10}$ solubilized with a non-toxic, solubilizing agent compatible with perfusion devices are particularly useful in transplantation methods and cardiac bypass surgery. When used in this way the perfusion solutions of the present invention provide improved solutions for maintaining the transplanted organ or by-passed organ from oxidative damage, ischemia and reperfusion injury during surgery.

The following examples are offered by way of illustration, not by way of limitation.

EXAMPLE 1

Male Wistar rats hearts were excised and perfused on a Life Sustainer™ 1000 (LS 1000) perfusion machine (Redmond, Wash.). Control rat hearts received a perfusate of polysorbate-80 diluted in Krebs-Henseleit solution at a flow rate of 1 milliliter per minute. The final concentration of polysorbate 80 was 2 microliters per one liter of Krebs-Henseleit solution (v/v). Isolated rat hearts were perfused for an additional 15 minutes while monitoring left ventricular function. LS 1000 perfusion was then interrupted by diverting perfusate flow away from the heart. An amount of perfusate sufficient to load the heart was administered followed by 30 minutes of complete ischemia. At the end of this period, perfusion flow was slowly established until perfusion pressures of approximately 80 mmHg were recorded. Control perfusate solution flow was re-established via syringe pump at a flow rate of 1 milliliter per ml. After two minutes of stabilization, a second left ventricular function study was carried out to compare pre- and post-ischemic Starling curve values.

An example of Starling curve values for a control rat heart (QP3-2702) is shown in the Table 1 which includes data for developed pressure (mm/Hg) before and after ischemia in rat hearts.

Treated rat hearts were subjected to the same procedure with the addition of 10 milligrams of Coenzyme $Q_{10}$ and 2 microliters of polysorbate-80 per liter of Krebs-Henseleit solution. Data were collected at the same times and in the same manner in order to compare pre- and post-ischemic Starling curve values for treated rat hearts (QP3-2701, QP3-3001, QP3-3002) is shown in Table 1 which includes data for developed pressure (mm/Hg) before and after ischemia in rat hearts.

The Starling curve data quantitatively demonstrate a protective effect of Coenzyme $Q_{10}$ solubilized with polysorbate-80 on rat hearts subjected to 30 minutes of ischemia injury. The control with polysorbate-80 alone did not provide this protective effect.

TABLE 1

|  | A | B | C | D | E[1] |
|---|---|---|---|---|---|
|  | Pre-Ischemia | | | | |
| QP3-2702 (control) | 61[2] | 78 | 149 | 152 | 155 |
| QP3-2701 | 58 | 81 | 76 | 86 | 92 |
| QP3-3001 | 61 | 163 | 169 | 188 | 190 |
| QP3-3002 (treated) | 51 | 102 | 135 | 141 | 139 |
|  | Post-Ischemia | | | | |
| QP3-2702 (Control) | 17 | 27 | 30 | 28 | 35 |
| QP3-2701[4] | 32 | 42 | 49 | 67 | N/A[3] |
| QP3-3001 | 86 | 127 | 151 | 163 | 179 |
| QP3-3002 (Treated) | 36 | 41 | 84 | 138 | 144 |

[1]Values A–D represent 50 microliter volume increases; A = 50, b = 100, C = 150, D = 200, E = 250
[2]Systolic/Diastolic difference in developed pressure (mm/Hg)
[3]N/A = Not Available
[4]Rat heart received a diluted amount of Coenzyme $Q_{10}$-Polysorbate 80.

Although the foregoing invention has been described in some detail by way of illustration and example for purposes of clarity of understanding, it will be obvious that certain changes and modifications may be practiced within the scope of the appended claims.

What is claimed is:

1. A composition for protecting mammalian organs from damage when isolated from the circulatory system, comprising a perfusion solution, about 10 mg/ml of Coenzyme $Q_{10}$ and about 2 $\mu l$ of a polysorbate per liter (v/v) compatible with an electrical/mechanical perfusion device.

2. The composition of claim 1, wherein the polysorbate is polysorbate-80 or polysorbate-20.

3. The composition of claim 1, wherein the perfusion solution comprises a cardioplegia solution or an organ preservation solution.

4. The composition of claim 3, wherein the cardioplegia solution comprises a blood-based cardioplegia solution.

5. The composition of claim 3, wherein the cardioplegia solution comprises Krebs-Henseleit solution, University of Wisconsin solution, St. Thomas II solution, Collins solution or Stanford solution.

6. The composition of claim 1, wherein the perfusion solution comprises Krebs-Henseleit solution, 10 mg Coenzyme $Q_{10}$ and 2 $\mu l$ of polysorbate-80 (v/v) per liter of perfusion solution.

7. A method for protecting organ tissues and cells from damage during isolation from the circulatory system comprising contacting the organ tissues and cells with a composition comprising a perfusion solution, about 10 mg/ml of Coenzyme $Q_{10}$ and about 2 $\mu l$ of a polysorbate per liter (v/v) compatible with an electrical/mechanical perfusion device.

8. The method of claim 7, wherein the polysorbate is polysorbate-80 or polysorbate-20.

9. The method of claim 7, wherein the perfusion solution comprises a cardioplegia solution or an organ preservation solution.

10. The method of claim 9, wherein the cardioplegia solution is a blood-based cardioplegia solution.

11. The method of claim 9, wherein the cardioplegia solution comprises Krebs-Henseleit solution, University of Wisconsin solution, St. Thomas II solution, Collins solution or Stanford solution.

12. The method of claim 7, wherein the perfusion device is a heart-lung machine.

13. The method of claim 7, wherein the organ tissue and cells are those of a mammalian heart.

14. The method of claim 13, wherein the heart tissue is a heart valve.

15. The method of claim 7, wherein the organ tissue and cells are those of a mammalian liver, kidney or lung.

16. The method of claim 7, wherein the organ is protected from ischemia or reperfusion injury.

17. The method of claim 7, wherein isolation from the circulatory system is during a transplant or an organ bypass surgery.

18. The method of claim 17, wherein the organ bypass surgery is a coronary bypass surgery.

19. A method for protecting organ tissues and cells form damage during isolation from the circulatory system comprising contacting the organ tissues and cells with a compositions comprising Krebs-Henseleit solution, 10 mg/l Coenzyme $Q_{10}$ and 2 $\mu$l polysorbate-80 per liter (v/v) perfusion solution.

* * * * *